United States Patent
Fukushima et al.

(10) Patent No.: US 9,486,496 B2
(45) Date of Patent: Nov. 8, 2016

(54) ANTI PERIODONTITIS-CAUSING MICROORGANISM AGENT AND MEDICAL OR DENTAL MATERIALS USING THE SAME

(75) Inventors: Tadao Fukushima, Fukuoka (JP); Tohru Hayakawa, Tokyo (JP); Yoshio Okahata, Kanagawa (JP); Makoto Mitarai, Ibaraki (JP); Keishi Iohara, Ibaraki (JP); Hiroyuki Enari, Ibaraki (JP); Haruchika Sekido, Ibaraki (JP)

(73) Assignees: MARUHA NICHIRO CORPORATION, Tokyo (JP); Tadao Fukushima, Fukuoka (JP)

( * ) Notice: Subject to any disclaimer, the term of this patent is extended or adjusted under 35 U.S.C. 154(b) by 14 days.

(21) Appl. No.: 13/140,931

(22) PCT Filed: Dec. 21, 2009

(86) PCT No.: PCT/JP2009/071231
§ 371 (c)(1),
(2), (4) Date: Jun. 20, 2011

(87) PCT Pub. No.: WO2010/071217
PCT Pub. Date: Jun. 24, 2010

(65) Prior Publication Data
US 2011/0257094 A1    Oct. 20, 2011

(30) Foreign Application Priority Data

Dec. 19, 2008  (JP) ................................ 2008-324524
Sep. 9, 2009   (JP) ................................ 2009-208631

(51) Int. Cl.
| | |
|---|---|
| A61K 38/16 | (2006.01) |
| A61K 31/713 | (2006.01) |
| C07K 14/435 | (2006.01) |
| C07H 21/04 | (2006.01) |
| A61P 19/08 | (2006.01) |
| A61K 38/17 | (2006.01) |
| A61K 6/033 | (2006.01) |
| A61K 47/48 | (2006.01) |

(52) U.S. Cl.
CPC .......... *A61K 38/1709* (2013.01); *A61K 6/033* (2013.01); *A61K 31/713* (2013.01); *A61K 47/48092* (2013.01); *C07H 21/04* (2013.01); *C07K 14/435* (2013.01)

(58) Field of Classification Search
None
See application file for complete search history.

(56) References Cited

U.S. PATENT DOCUMENTS

| | | | | |
|---|---|---|---|---|
| 7,204,874 | B2 * | 4/2007 | Jia et al. ................ | 106/35 |
| 7,758,892 | B1 * | 7/2010 | Chen et al. ............. | 424/497 |
| 2007/0003538 | A1 | 1/2007 | Madhyastha | |
| 2008/0139450 | A1 | 6/2008 | Madhyastha et al. | |

FOREIGN PATENT DOCUMENTS

| | | |
|---|---|---|
| EP | 1906736 A1 | 4/2008 |
| JP | 61-115030 A | 6/1986 |
| JP | 63-65872 A | 3/1988 |
| JP | 64-34371 A | 2/1989 |
| JP | 1-202072 A | 8/1989 |
| JP | 2-241460 A | 9/1990 |
| JP | 8-239398 A | 9/1996 |
| JP | 11-228526 A | 8/1999 |
| JP | 2001-89436 A | 4/2001 |
| JP | 2001-321123 A | 11/2001 |
| JP | 2001-327591 A | 11/2001 |
| JP | 2005-289852 | * 10/2005 |
| JP | 2005-289852 A | 10/2005 |
| JP | 2007-97884 A | 4/2007 |
| JP | 2007-169201 A | 7/2007 |
| JP | 2008-110952 A | 5/2008 |
| JP | 2008110952 A | 5/2008 |
| JP | 2008-133253 A | 6/2008 |
| JP | 2008-546812 T | 12/2008 |
| WO | 2007/003028 A1 | 1/2007 |
| WO | 2008/141416 A1 | 11/2008 |

OTHER PUBLICATIONS

Fukushima et al., J. Oral Tissue Engin., 2008, vol. 6(1):24-32.*
Kontani et al., Infection and Immunity, 1999, vol. 67(9):4917-4920.*
Kontani, et al., "Inhibitory Effects of Protamines on Proteolytic and Adhesive Activities of Porphyromonas gingivalis", American Society for Microbiology, Infection and Immunity, pp. 4917-4920 (1999).
International Search Report for International Application No. PCT/JP2009/071231 mailed Feb. 2, 2010 with English translation.
Taiwanese Office Action, Notice of Examination Opinion for Taiwanese Patent Application No. 098143881, date of notice of Sep. 27, 2012, with partial English translation.
Office Action for Japanese Patent Application No. 2009-208631, dated Apr. 13, 2011, with partial English translation.
Watanabe, Kiyoshi, et al. "Effects of protamine on osteoblastic MC3T3-E1 cells", Jap. J. Oral Biol., 27: pp. 989-991, 1985.
Data Base WPI Week 200241, Thomson Scientific, London, GB corresponding to Ref. No. X-002738614.
Extended European Search Report corresponding to Application No. 09833518.5-1464/2377545, PCT/JP2009/071231; Date of Mailing: Apr. 29, 2015.

* cited by examiner

*Primary Examiner* — Xiaozhen Xie
(74) *Attorney, Agent, or Firm* — Cantor Colburn LLP

(57) ABSTRACT

A medical or dental material can be prepared by using, as an active ingredient, at least one of a protamine, and derivatives thereof and hydrolysates thereof, or a complex of at least one of a protamine, and derivatives thereof and hydrolysates thereof with an anionic high molecular weight compound. As a result, an antibacterial agent against periodontal disease-causing bacteria can be provided, which is highly safe without concern of a side effect. A medical or dental material can be also provided, which exhibits antimicrobial activity on periodontal disease-causing bacteria and additionally has insolubility in water and good formability.

5 Claims, 4 Drawing Sheets

(A)  (B)

(A)

(B)

(A)

(B)

ANTI PERIODONTITIS-CAUSING MICROORGANISM AGENT AND MEDICAL OR DENTAL MATERIALS USING THE SAME

This is a U.S. national stage application of International Application No. PCT/JP2009/071231, filed on Dec. 21, 2009. Priority under 35 U.S.C. 119(a) and 35 U.S.C. 365(b) is claimed from Japanese Application Nos. 2008-324524, filed Dec. 19, 2008, and JP2009-208631, filed Sep. 9, 2009, the disclosure of each of which are also incorporated herein by reference.

TECHNICAL FIELD

The present invention relates to an antibacterial agent against periodontal disease-causing bacteria containing a protamine, a derivative thereof, or a hydrolysate thereof, exhibiting an activity to inhibit growth of periodontal disease-causing bacteria, as well as an antibacterial agent against periodontal disease-causing bacteria, and a medical or dental material, which contain a complex formed with the protamine, etc. and an anionic high molecular weight compound.

BACKGROUND ART

Periodontal diseases develop, which is cased by factors possessed by a host or life habits such as smoking of the host, in addition to participation of a plurality of periodontal disease-causing bacteria. It is said that approximately 80% of Japanese adults are suffering. It is reported that periodontal diseases not only deteriorate quality of life (QOL) by masticatory function disorder caused by decrease of the supporting function of teeth or loss of teeth, but also constitute risk factors for systemic diseases, such as cardio-circulatory diseases (endocarditis, coronary heart disease), pneumonia, and preterm delivery or low-weight birth. Consequently, the roles of prevention and treatment of periodontal diseases are very important not only for improvement of the QOL of people in Japan or else, where aging is progressing remarkably, but also for clinical practices.

The direct cause of a periodontal disease is periodontal disease-causing bacteria per se or a protease produced by disease-causing bacteria, which causes gingivitis and may eventually extend the inflammation to paradentium advancing to periodontitis. Most of periodontal disease-causing bacteria are Gram-negative obligatory anaerobic bacteria, and examples of typical disease-causing bacteria include *Porphyromonas gingivalis*, *Treponema denticola*, *Tannerela forsythensis*, *Prevotella intermedia*, and *Aggregatibacter actinomycetemcomitans*.

As antibacterial agents against such periodontal disease-causing bacteria, β-lactam containing agents, macrolide containing agents, and quinolone containing agents are currently used. However, they have specific characteristics in their antibacterial activities, respectively, and, therefore, an appropriate antibacterial agent should be selected or used in a combination depending on a kind of a disease-causing bacterium or the stage of progression of a periodontal disease. Meanwhile, a problem of a side effect may break out, in case the dosage or the number of doses should increase. Consequently, practical mainstream treatments for periodontitis are mechanical removal of plaque, dental calculus, endotoxin on root surfaces, etc. and surgical ablation of an inflamed tissue. Thus, administration of an antibacterial agent is conducted only as a supportive treatment, except at an acute insult of periodontitis.

Under such circumstances, it has been reported that protamine, which is a basic protein obtainable from a testis of fishes (milt), exhibits inhibitory activity on Arg-gingipain, which is a protease produced by *Porphyromonas gingivalis* (see Kontani M, and 5 coauthors, "Inhibitory Effects of Protamines on Proteolytic and Adhesive Activities of *Porphyromonas gingivalis*", Infection And Immunity, 1999, vol. 67, issue 9, p. 4917-4920). Further, it has been disclosed that periodontitis by periodontal disease-causing bacteria can be effectively inhibited by combining tranexamic acid and/or ε-amino caproic acid with protamine or derivatives thereof (see Japanese Patent Laid-Open No. 2007-169201). The protamine is generally used as a food preservative and highly safe, and consequently has promise as a pharmaceutical alternative to a conventional antibacterial or antibiotic.

Meanwhile, it has been disclosed that protamine exhibits an inhibitory effect against growth of *Streptococcus mutans*, which is a caries-causing bacterium (see Japanese Patent Laid-Open No. 228526/99), and an inhibitory effect against attachment of oral bacteria (see Japanese Patent Laid-Open No. 2001-89436). Further, the present inventors have found that hydrolysates of a protamine exhibit antifungal activity against fungi such as those belonging to the genus *Candida*, which cause oral candidiasis (see Japanese Patent Laid-Open No. 2008-133253).

As described above, although it is known that protamine or derivatives thereof exhibit not only antimicrobial activity but also inflammation inhibitory activity on periodontal diseases, the growth inhibitory activity on periodontal disease-causing bacteria per se has not been known yet. Further, since protamine is water-soluble, protamine has been considered to have difficulty to maintain its growth inhibitory activity on periodontal disease-causing bacteria for a long period of time in the oral cavity.

Meanwhile, protamine is a kind of polycations, and it is known that it forms a complex insoluble in water by binding electrostatically with an anionic high molecular compound.

DNAs obtained from testis of fishes similarly to protamine have a large number of phosphate groups in their molecule, which have function as anionic bond elements. Therefore, DNAs exhibit electrostatic affinity for a cationic substance, which can form an electrostatic reaction product with such cationic substance. A DNA molecule is in nature poor in formability and water-soluble, and, consequently, it is difficult to control the in vivo metabolic diffusion speed. It has been disclosed (see Japanese Patent Laid-Open No. 239398/96), however, that a water-insoluble, self-supporting transparent film can be prepared by binding electrostatically a DNA molecule with a cationic artificial lipid.

In the DNA/lipid complex film disclosed in the above patent publication, the DNA molecules as a biopolymer can maintain an orderly double helix structure, to which various low molecular weight compounds can be intercalated in gaps between DNA bases in the double helix structure, or similar low molecular weight compounds can be bound by groove binding in two grooves of the DNA (major groove, minor groove). The above patent publication further discloses a process for producing a medical material by intercalation and/or groove binding of an active pharmaceutical ingredient has been invented (see Japanese Patent Laid-Open No. 2001-327591).

Paying attention to the fact that chitosan, which has been utilized as a medical and/or dental material, is a cationic substance, the present inventors have invented a complex of a DNA molecule and chitosan holding the double helix structure specific to the DNA. Thus, the complex is water-insoluble, and has bio-compatibility, an antimicrobial property, and good formability (see Japanese Patent Laid-Open No. 2005-289852). Further, a process for forming easily a DNA/chitosan complex to a fibrous, spherical, or disk-like form by suspending the same in a phosphate buffer solution (see Japanese Patent Laid-Open No. 2007-97884), and a process for forming a film by press-molding the same under heating (see Japanese Patent Laid-Open No. 2008-110952) have been invented. Since the DNA/chitosan complex and the formed products thereof have excellent biocompatibility and bio-stability, they have had promise as medical and/or dental materials.

However, such problems have become known including the recognized formation of neutrophil, when a DNA/chitosan complex was implanted subcutaneously in a rat, at an initial stage of the implanting probably due to an acute inflammatory reaction; and inadequate activity as an antibacterial or an antibiotic. Consequently, a complex with a cationic substance exhibiting better biocompatibility and antimicrobial activity than chitosan has been desired. Especially in the dental field, development of a material having antimicrobial activity on periodontal disease-causing bacteria has been desired.

SUMMARY OF THE INVENTION

Technical Problems to be Solved by the Invention

The present invention has been conducted in view of the above described states of the conventional art. The first object of the present invention is to provide an antibacterial agent against periodontal disease-causing bacteria which is highly safe without concern of a side effect. The second object of the present invention is to provide a dental material and/or a medical material which exhibits antimicrobial activity on periodontal disease-causing bacteria and additionally has insolubility in water and good formability as well as high biocompatibility.

Means for Solving the Problems

With respect to the first invention as the present invention (hereinafter referred to as "the first present invention"), the present inventors have intensively studied to find that a protamine or derivatives thereof and hydrolysates thereof exhibit antimicrobial activity on periodontal disease-causing bacteria. Since a protamine has been utilized practically as a food preservative, and known of high safety for the human body, they are found to be suitable for preventing and treating periodontal diseases as a material, which can be replaced for the conventional antibacterials and antibiotics.

With respect to the second invention as the present invention (hereinafter referred to as "the second present invention"), the present inventors have found that a complex of a protamine or a derivative thereof and a hydrolysate thereof with an anionic high molecular weight compound exhibits antimicrobial activity on periodontal disease-causing bacteria, and additionally has insolubility in water and good formability, and that the complex is suitable for preventing and treating periodontal diseases effectively in the oral cavity for a long period of time, thereby completing the second present invention.

With respect to the third invention of the present invention (hereinafter referred to as "the third present invention"), the inventors have paid attention to the DNA as an anionic high molecular compound according to the second present invention, and found that the complex exhibits such antimicrobial activity, which has not been achieved by the conventional compounds with a DNA, and that the complex has high biocompatibility and promises to provide a dental material and/or a medical material.

Namely, an antibacterial agent against periodontal disease-causing bacteria according to the first present invention comprises at least one of a protamine or a derivative thereof and a hydrolysate thereof as an active ingredient, which exhibits an inhibitory activity against the growth of the periodontal disease-causing bacteria.

An antibacterial agent against periodontal disease-causing bacteria according to the second present invention comprises a complex of a least one of a protamine or a derivative thereof and a hydrolysate thereof, as an active ingredient, with an anionic high molecular compound, which are electrostatically bound, wherein the complex has insolubility in water and formability, and exhibiting an inhibitory activity against the growth of the periodontal disease-causing bacteria.

The medical or dental material according to the third present invention is characterized by comprising a complex of a least one of a protamine or a derivative thereof and a hydrolysate thereof, as an active ingredient, with an anionic high molecular compound, which are electrostatically bound, wherein the complex has insolubility in water and formability, and exhibiting an inhibitory activity against the growth of the periodontal disease-causing bacteria.

Effects of the Invention

According to the present invention, the agent inhibits directly the growth of periodontal disease-causing bacteria in the oral cavity and the agent has high safety for the human body. Therefore, the present invention can provide an antibacterial agent against periodontal disease-causing bacteria effective for preventing and treating periodontal diseases. Further, since the compound with an anionic high molecular compound is water-insoluble and excellent in formability, the growth of periodontal disease-causing bacteria can be effectively inhibited in the oral cavity for a long period of time.

Since a protamine/DNA complex among the complexes according to the present invention is superior in biocompatibility and in vivo stability, and additionally superior especially in formability, it can be used for a periodontal guided tissue regeneration (GTR) membrane, a guided bone regeneration (GBR) technique, an antimicrobial denture coating material, an oral cavity antibacterial agent, a hemostatic agent and other various sanitary goods. Further, since the protamine/DNA complex can include a low molecular weight compound(s) by intercalation or groove binding, it can be utilized as a membrane, a film, a lining material, or a coating material for a delivery system (DDS), which carries, delivers and supplies a pharmaceutical(s), such as a growth factor (b-FGF, BMP, etc.) and an antibiotic, to a target site such as an affected part. It can be used not only as a dental material, but also used as a wide variety of medical materials, such as a scaffold material for regenerative medicine, a wound dressing, an infection prevention membrane, an adhesion prevention membrane, and a grafting material.

DESCRIPTION OF THE EMBODIMENTS

Figure 1:
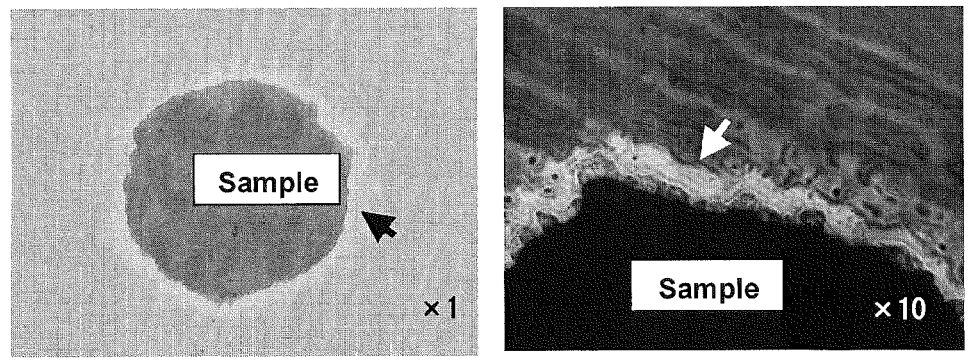
FIG. 1 shows an inhibition zone formed by a protamine/DNA complex against *Staphylococcus aureus*.
Figure 2:
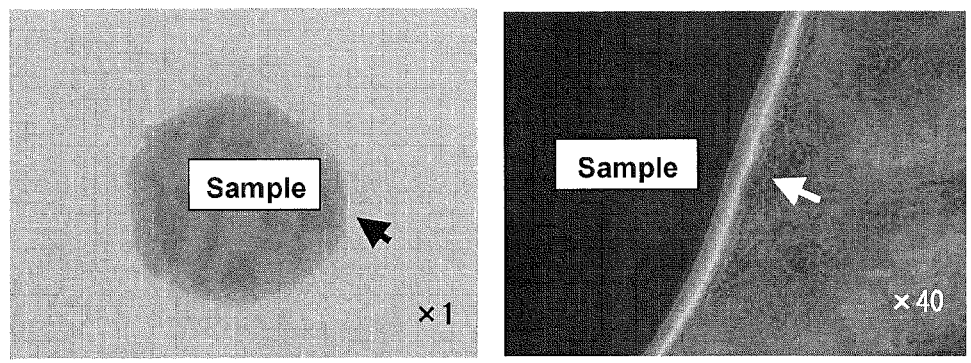
FIG. 2 shows an inhibition zone formed by a protamine/DNA complex against *Escherichia coli*.
Figure 3:
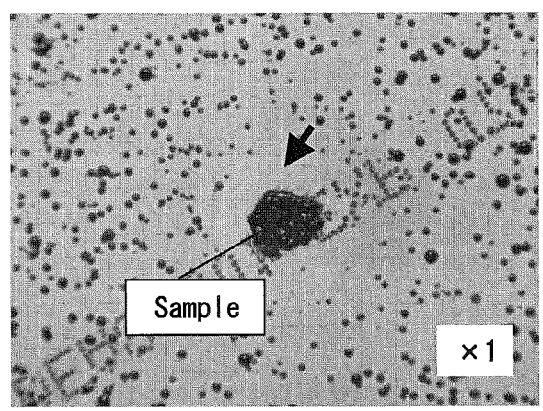
FIG. 3 shows an inhibition zone formed by a protamine/DNA complex against a periodontal disease bacterium (*Porphyromonas gingivalis*).
Figure 4:
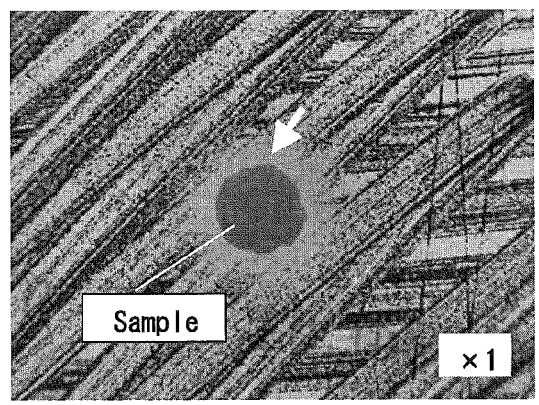
FIG. 4 shows an inhibition zone formed by a protamine/DNA complex against a periodontal disease bacterium (*Prevotella intermedia*).

Next, the present invention will be described in detail below.

A protamine or derivatives thereon and hydrolysates thereof exhibit antimicrobial activity on at least one of periodontal disease-causing bacteria represented by *Porphyromonas gingivalis* and *Prevotella intermedia*. They can provide effects of prevention, relief and treatment of periodontal diseases by using them as an antibacterial agent against periodontal disease-causing bacteria in the oral cavity.

A protamine is a strongly basic protein existing as a nucleoprotamine bonded with a DNA in a sperm nucleus of fish, such as salmon, herring and trout, and referred to as salmine (from salmon), clupeine (from herring), etc. according to difference in their sources. They have slightly different structures respectively, but any of the protamines can be utilized.

The term "a protamine derivative" refers to a salt of a protamine with an inorganic acid or an organic acid, or a salt with an inorganic base or an organic base. Depending on the intended use of the salt, an acid or a base may be selected, and in view of the uses such as foods, cosmetics, and pharmaceuticals, the following pharmaceutically acceptable salts are preferable. Namely, examples of an acid addition salt include a hydrochloride, a nitrate, a sulfate, a methanesulfonate, a p-toluenesulfonate, as well as a salt with a dicarboxylic acid, such as oxalic acid, malonic acid, succinic acid, maleic acid, and fumaric acid, and a salt with a monocarboxylic acid, such as acetic acid, propionic acid, and butyric acid. Examples of an inorganic base suitable for forming a salt of a peptide compound to be obtained according to the present invention include hydroxides, carbonates, and bicarbonate of ammonia, sodium, lithium, calcium, magnesium, and aluminium. Examples of a salt with an organic base include a salt of a mono-, di- or tri-alkylamine, such as methylamine, dimethylamine, and triethylamine; mono-, di- and tri-hydroxyalkylamine salts; a guanidine salt; and an N-methylglucosamine salt.

Hydrolysates of a protamine are prepared by hydrolyzing a protamine using an acid, an alkaline substance, a protease, or a combination thereof. Hydrolysis using a protease is preferable. A more detailed process of the hydrolysis is as follows. Deionized water is added to a protamine, and then the pH is adjusted to the optimum pH for an enzyme by adding sodium hydroxide or hydrochloric acid. After heated up to the optimum temperature for the enzyme, the enzyme is added and the enzymatic reaction is conducted with stirring. After the completion of the reaction, the reaction liquid is heated to 80° C. to 100° C. for 5 min to 60 min for deactivation by heat, the pH is adjusted to a neutral zone, and then the reaction liquid is freeze-dried to yield decomposition products of the protamine.

With respect to the decomposition products of a protamine prepared according to the above process, a completely decomposed protamine exhibits almost no antimicrobial activity. Consequently, it should preferably be partially decomposed, so that their molecular weights distribute in the range of 500 to 4,000.

Examples of a protease usable for hydrolysis of a protamine include enzymes produced by bacteria belonging to genus *Bacillus*, such as *Bacillus subtilis*, *Bacillus thermoproteolyticus*, and *Bacillus licheniformis*; enzymes produced by molds belonging to genus *Aspergillus*, such as *Aspergillus oryzae*, *Aspergillus niger*, and *Aspergillus mellens*; and enzymes produced by molds belonging to genus *Rhizopus*, such as *Rhizopus niveus*, and *Rhizopus delemar*, as well as pepsin, pancreatin, and papain. The enzymes may be used singly or in combination of two or more enzymes. The protease is classified into an endopeptidase, which cleaves a protein through specific recognition site(s) of an internal sequence of the same, and an exopeptidase, which cleaves every 1 or 2 terminal amino acid residues. Therefore, according to need, various peptide chains can be yielded by a combination of an endopeptidase and an exopeptidase. In the case of hydrolysis by an enzyme, 0.001% to 10% of the enzyme is added with respect to a substrate, and the solution is adjusted to the optimum pH for the enzyme(s) to be used, and then hydrolyzed.

In an antibacterial agent against periodontal disease-causing bacteria according to the present invention, at least one of a protamine or derivatives thereof, and hydrolysates thereof is used as an active ingredient. The antibacterial agent can be optionally provided as a composition by combining with a component(s) selected from carriers, diluents and auxiliary components such as various additives. The carrier(s) and the auxiliary component(s) combined in the antibacterial agent against periodontal disease-causing bacteria, which are typically pharmaceutically acceptable depending on the intended purposes, can be different according to the intended purposes and forms of the agent.

Examples of the carriers and auxiliary components include water, various organic solvents, and various buffer solutions, as well as a filler, an extender, a binder, a humectant, a surfactant, an excipient, a colorant, and a fragrance.

Further, an antibacterial agent against periodontal disease-causing bacteria according to the present invention can take a form of a complex prepared as an electrostatic reaction product of at least one active ingredient of a protamine, derivatives of a protamine and hydrolysates of a protamine with an anionic high molecular weight compound. The complex has antimicrobial activity on periodontal disease-causing bacteria, as well as insolubility in water and formability. A medical or dental material can be prepared using the complex.

The anionic high molecular weight compound to be used as a starting material for the above described complex may be selected from alginic acid, an alginic acid salt or an alginic acid derivative, DNA, RNA, pectin, carrageenan, gellan gum; a polycarboxylic acid, such as carboxymethylcellulose, carboxymethylamylose; an anionic polyamino acid such as polyglutamic acid; carboxymethyl starch; hyaluronic acid; polyacrylic acid; and polymethacrylic acid; a polysulfate, such as dextran sulfate, heparin, heparan sulfate, chondroitin sulfate, keratan sulfate, dermatan sulfate and potassium polyvinyl sulfate. One or more of the above compounds may be selected. Examples of an alginic acid salt or an alginic acid derivative include sodium alginate, propyleneglycol alginate, and oligo-alginate, without limited thereto.

A complex with a DNA among others as an anionic material holds the double helix structure(s) specific to the DNA at least a part of the DNA as the component of the complex and has substantially no solubility in water. Since the complex has biocompatibility in addition to the above properties, the complex is especially a preferable material as a medical or dental material.

As a DNA, both a DNA of a natural origin and a synthetic DNA can be used. Examples of a DNA of a natural origin include a λ phage DNA of a bacterial virus, an *Escherichia coli* chromosome DNA, a calf thymus DNA, and a sperm DNA of fish, such as salmon, herring, and trout. Examples of a synthetic DNA include various synthetic DNAs having different nucleotide sequences obtained by synthesis in a synthesis device using poly(dA), poly(dT), poly(dG), poly (dC), poly(dA-dT), poly(dG-dC), etc. Examples include various synthetic RNAs having different nucleotide sequences obtained by synthesis in a synthesis device using poly(A), poly(T), poly(G), poly(U), poly(A-T), poly(G-U), etc. Examples include a DNA/RNA hybrid having complementary base pairs obtained by synthesis in a synthesis device using a DNA/RNA hybrid of poly(dG), poly(U), poly(G), poly(dC), poly(dA-dT), poly(A-T), etc. They may be used singly or in a combination according to need.

There is no particular restriction on the molecular weight of a DNA, insofar as a double helix structure is maintained to intended extent. With respect to the molecular weight of a DNA, a DNA with 10 bp to 30,000 bp can be used. In case the molecular weight is too high, the preparation of an aqueous solution becomes difficult; while, in case the molecular weight is too low, the recovery rate of a complex becomes low. Therefore, the use of a DNA having the center of the molecular weight distribution between 300 bp and 7,000 bp is preferable.

Such DNA has a structure having various groups, such as groups carrying a phosphoric acid-containing group at their terminals, which bind with the four kinds of the bases [cytosine (C), guanine (G), adenine (A), and thymine (T)] forming the double helix structure. Such DNA expresses anionic property, on the whole, due to, for example, the above phosphate groups etc bonded to terminals.

Such DNA itself has a string-like shape with a double helix structure. Since the DNA is soluble in water, the DNA itself is lacking formability. Taking advantage of the anionic property of the DNA, a DNA/polycation complex can be obtained by reacting electrostatically the anionic DNA and a cationic polycation compound. By forming such a complex, the DNA becomes practically insoluble in water. Further, the solubility in an organic solvent becomes also lower.

A complex using a DNA as an anionic material can be prepared by reacting a DNA with at least one of a protamine, derivatives of a protamine and hydrolysates of a protamine in an aqueous medium. For example, such reaction can be carried out by adding an aqueous solution of a DNA to a stirred aqueous solution of a protamine followed by mixing.

The mixing ratio of a DNA to at least one of a protamine, derivatives of a protamine and hydrolysates of a protamine can be selected according to an intended use of the complex. It can be selected within, for example, a range of 1/9 to 9/1, and preferably 1/1 to 1/1.5 (weight ratio).

The complex can be formed as precipitate by reacting a DNA with at least one of a protamine, derivatives of a protamine and hydrolysates of a protamine in an aqueous medium. The precipitate thus obtained is washed with water or various buffer solutions. The precipitate is further washed with water according to need. Excess water is then removed by centrifugation, etc. followed by drying, and a dry complex can be thus obtained. A process for drying may be appropriately selected and used according to an intended purpose from a normal temperature drying process, a heat-drying process, a freeze-drying process, and a reduced-pressure drying.

A buffer solution for washing a precipitate may be selected from a Tris buffer solution, a borate buffer solution, a HEPES buffer solution, an acetate buffer solution, a citrate buffer solution, a glycine buffer solution, a barbiturate buffer solution, a phthalate buffer solution, a cacodylate buffer solution, a carbonate buffer solution, a Bis-Tris buffer solution, a Bis-Tris propane buffer solution, an MES buffer solution, an ADA buffer solution, a PIPES buffer solution, an ACES buffer solution, a cholamine chloride buffer solution, a BES buffer solution, an MOPS buffer solution, a TES buffer solution, an HEPPS buffer solution, a Tricine buffer solution, a glycinamide buffer solution, a bicine buffer solution, a TAPS buffer solution, a CHES buffer solution, a CAPS buffer solution, a phosphate buffer solution, etc. The concentration and the pH of a buffer solution may be freely selected so as to obtain a DNA/protamine complex with the desired attributes and properties.

A dried complex thus obtained can be formed into various shapes, such as a paste form, a gel form, a glue form, a string form, a rod form, a spherical form, a disk form, and a film form, according to an intended purpose, and used. The dried complex may be optionally ground for the above formulation. Since the double helix structure of the DNA is maintained almost completely without destruction, the functions of the DNA can be used stably and efficiently by using the complex.

A complex using a DNA as an anionic material can be brought into various easily formable forms, such as a paste form, a gel form, and further a sticky glue form, by adding, for example, an appropriate amount of water and kneading the mixture in a mortar, wherein the kneading duration is modified according to the respective form.

A complex using a DNA as an anionic material in a paste form can be extruded using a syringe into a phosphate buffer solution to produce a formed product in a string form. Further, a molded product in various forms, such as a rod form, a spherical form and a disk form, can be easily obtained by filling the paste into a mold suitable for an intended purpose.

A formed product in a film form of a complex using a DNA as an anionic material can be obtained by pressing a dry powder of the complex, or formed product in a paste form, a rod form, or a disk form by using a heated forming machine. Further, a transparent film can be easily formed by extending thinly the formed product of a protamine/DNA complex in a mortar.

The temperature during the formation of a film using the heated forming machine can be set variously depending on a material for forming a film. The temperature can preferably be selected within a range between room temperature (e.g. 15° C. to 25° C.) and 120° C. The pressing pressure during the film formation can be selected within a range between 2 MPa and 20 MPa. The pressing time duration is selected so as to obtain required properties of the film. When the above temperature and pressing pressure are used, the film formation can be completed, for example, within 1 min to 10 min. Preferably by pressing for 5 min to 10 min a tough and unbreakable film can be formed. The film thickness can be regulated by the temperature, the pressure, and the pressing time duration during pressing. A transparent complex film with a film thickness of about 1 μm to 100 μm can be obtained according to the above process.

A dental material according to the present invention can be used as a membrane for a guided tissue regeneration (GTR) technique for regenerating a lost paradentium. A dental material containing a complex using a DNA as an anionic material is especially superior in bio-compatibility and more preferable as a material for a GTR membrane. A GTR membrane is a material to set up an environment for regenerating alveolar bone, periodontal ligament, cementum, etc. by blocking and separating the environment against the precedent proliferation of the epithelial tissue at the defective site. Since the membrane is kept in a living body for a certain period of time, it should preferably be composed of a material with high bio-compatibility, further preferably have an antimicrobial property against periodontal disease-causing bacteria, etc. As such a membrane, an absorbable membrane using collagen or polylactic acid as a base material, and a nonabsorbable membrane using a fluorocarbon resin, have been used. A GTR membrane comprising a formed product of a complex using a DNA as an anionic material according to the present invention in a film form, a gel form, or a glue form, has high bio-compatibility and can be used stably for a longer period of time than a conventional membrane. Further, using a GTR membrane produced from a dental material according to the present invention, the regeneration period can be set at a longer period than the conventional absorbable membrane.

Further, a dental material according to the present invention can be used as an antimicrobial coating agent or a washing agent for an artificial tooth etc. by forming a formed product, for example, in a paste form, a gel form, or a glue form. Since a complex containing a DNA as an anionic material is especially superior in stability in vivo, it can exhibit antimicrobial activity against periodontal disease-causing bacteria for a longer period than a conventional denture coat.

With respect to a complex containing a DNA as an anionic material, a part of phosphate groups, as the anionic groups of the DNA, electrostatically binds to the cationic groups of a protamine so as to exhibit desired formability, while many phosphate groups remain as they are, i. e., they are not bound with the protamine. A bone morphogenetic factor or a growth factor can be bound electrostatically with the DNA by effectively using such free phosphate groups of the DNA so that the complex can be used also as a carrier of a cytokine or an antibiotic. Further, the complex can be used also as a drug carrier by using intercalation or groove binding by a double helix structure of the DNA.

Any bone morphogenetic factors and growth factors can be used without particular restriction, insofar as they can be carried by the complex containing the DNA as an anionic material. Examples of the bone morphogenetic factors include bone morphogenetic protein (BMP), and recombinant human bone morphogenetic protein (rhBMP). Examples of the growth factors include fibroblast growth factor (FGF), transforming growth factor beta (TGF-β), epidermal growth factor (EGF), insulin-like growth factor (IGF), platelet-derived growth factor (PDGF), vascular cell growth factor (VEGF), and neurotrophic factor (NGF). At least one of the above substances can be used.

A complex containing a DNA as an anionic material can be mixed with powdery or granular calcium phosphate by kneading or otherwise to obtain a mixture having formability. During the preparation of the mixture, an appropriate amount of water or a phosphate buffer solution may be added according to need to obtain a paste with formability. Calcium phosphate in a form of granule or powder becomes formable. More particularly, a kneaded mixture of the complex containing the DNA as an anionic material and calcium phosphate in a form of granule or powder can be formed into any form by packing the mixture into a mold, or packed in a bone defective part with a complicated shape by extrusion from a syringe filled with the mixture. Further, after a mixture paste is formed into a desired shape, the shaped paste can be subjected to a drying treatment to fix the desired shape of the mixture. The mixture can be used for applications as a regeneration inducting agent or a regeneration promoting agent for a paradentium (specifically, alveolar bone, periodontal ligament, and cementum) in a paradentium regeneration therapy, or as a bone filling material for inducing or promoting osteogenesis at a bone defective part. However, the applications of the mixture are not limited.

Examples of the calcium phosphate materials include hydroxyapatite (HA), tricalcium phosphate (α-TCP, β-TCP), calcium hydrogen phosphate dihydrate (DCPD), octacalcium phosphate (OCP), tetracalcium phosphate (TeCP), and carbonate apatite (CAP). At least one of these materials can be used.

The complex containing the DNA as an anionic material can be formed not only as the above described dental material, but also as a film, a lining material or a coating material, which can be used as a scaffold material for regenerative medicine, a wound dressing, an infection prevention membrane, and an adhesion prevention membrane. Thus, the complex can be used as a medical material characterized by improving the bio-compatibility on the occasion of transplantation, or suppressing the biological reaction to a xenobiotic.

EXAMPLES

Best modes for carrying out the present invention will be described in detail referring to Examples, provided that the present invention be not limited to the following Examples. A microbe and a cell used in the following Examples are available publicly. For example, *Prevotella intermedia* (ATCC25611), *Porphyromonas gingivalis* (ATCC33277), mouse-derived fibroblast L-929 (Example 3), MC3T3-E1 cell (mouse-derived osteoblast-like cell; Example 5) can be also publicly available from a cell line, microorganism strain, gene bank at Summit Pharmaceuticals International Corporation.

Example 1

Antimicrobial Activity of Protamine Hydrochloride, and Hydrolysates Thereof on Periodontal Disease-Causing Bacteria (a) Samples Protamine hydrochloride (Proserve; by Maruha Nichiro Foods, Inc.) originated from milt of chum salmon (*Oncorhynchus keta*), hydrolysates (HAP100; by Maruha Nichiro Foods, Inc.) of the protamine hydrochloride by Bromelain (by Amano Enzyme Inc.), and hydrolysates (Thermoase hydrolysate) of the same protamine hydrochloride by Thermoase (by Amano Enzyme Inc.) were used as samples. The Thermoase hydrolysate was prepared by adding 80 mL of deionized water to 50 g of Proserve (by Maruha Nichiro Foods, Inc.), followed by addition of sodium hydroxide to adjust the pH to 8.0; then the mixture was heated to 65° C., to which 0.4 g of Thermoase (by Amano Enzyme Inc.) was added to carry out the enzymatic reaction with stirring for 2 hours. After the completion of the reaction, the reaction liquid was heated to 95° C. for heat deactivation for 30 min. After the pH of the reaction liquid was adjusted to 8.5, the reaction liquid was freeze-dried. The weight-average molecular weight (Mw) of the Thermoase hydrolysate was 3,587 Da.

(b) Method for Determining Antimicrobial Activity

A series of diluted solutions of a sample with purified water by repeating 2-fold (w/v) dilution was prepared. Each diluted solution was sterilized for dissolving the sample and 1/9 of each diluted solution was added to a PEA added Brucella HK Agar medium (by Kyokuto Pharmaceutical Industrial Co., Ltd.) kept its temperature at 50±1° C. After each mixture was thoroughly mixed and dispensed into plates to prepare a sample plate for measurement of sensitivity by solidifying the mixture in the plates. Next, *Porphyromonas gingivalis* JCM8525 was cultured anaerobically on an enrichment medium at 37±1° C. for 5 to 7 days, and then the bacterial count was adjusted to about $10^6$ cfu (colony forming unit)/mL with a GAM broth medium (by Nissui Pharmaceutical Co., Ltd.) to prepare an inoculum.

The inoculum was streaked approximately 2 cm on each plate for sensitivity measurement using a resin loop (inner diameter: about 1 mm), and cultured anaerobically at 37±1° C. for 5 to 7 days. After the culturing for a pre-determined period of time, the minimum inhibitory concentration (MIC) was determined as the least concentration required for inhibiting the bacterial growth.

(c) Test Results

The results of MIC are shown in Table 1. As a result, MICs of the hydrolysates of the protamine (Bromelain hydrolysate and Thermoase hydrolysate) were 1,250 ppm and MIC of the protamine (Proserve) was 625 ppm. Proserve exhibited higher activity than the hydrolysates.

TABLE 1

Minimum concentration (MIC) for inhibition of bacterial growth of the tested bacterium

| Tested bacterium | Test sample | MIC (ppm) |
| --- | --- | --- |
| *Porphyromonas gingivalis* | Proserve | 625 |
| | HAP100 (Bromelain hydrolysate) | 1,250 |
| | Thermoase hydrolysate | 1,250 |

Example 2

Antimicrobial Activity of Protamine/DNA Complex (a) Samples

An aqueous solution of a protamine sulfate originated from milt of chum salmon (Proserve; by Maruha Nichiro Foods, Inc.) at a concentration of 57% (w/v), and an aqueous solution of a DNA also originated from milt of chum salmon (the center of the molecular weight distribution of 300 bp; by Maruha Nichiro Foods, Inc.) at a concentration of 0.5% (w/v) were used. In order to make the respective weights of the protamine sulfate and the DNA to 1:1, 0.875 g of the aqueous solution of a protamine sulfate was diluted by 100 mL of sterile distilled water and mixed with 100 mL of the DNA solution, and stirred for 1 hour. Precipitate was recovered by centrifugation, washed with water, and centrifuged again to recover the precipitate thus washed as a protamine/DNA complex (undried). The protamine/DNA complex (undried) was further freeze-dried to yield 0.61 g of a protamine/DNA complex. The recovery rate of the protamine/DNA complex was 61 weight-% (w/w). The sample was ground and, after adding an appropriate amount of water, packed into a mold. After removing it from the mold, it was freeze-dried again and a disk-form sample with a diameter of about 5 mm, and a thickness of about 1 mm was prepared therefrom.

(b) Evaluation Method for Antimicrobial Property

An antimicrobial test was conducted qualitatively by a growth inhibition zone formation test, in which a sample was left sitting on the surface of a medium of agar, etc. to which a tested bacterium solution was uniformly applied. Existence or nonexistence of growth inhibition was observed. Tested bacteria for evaluating antimicrobial property were *Staphylococcus aureus*, *Escherichia coli*, and periodontal disease-causing bacteria (*Porphyromonas gingivalis* and *Prevotella intermedia*). They are all publicly available.

(c) Test Results

The test results are shown in FIGS. 1 to 4. Against *Staphylococcus aureus*, a growth inhibition zone of the bacterium was observed around the protamine/DNA complex sample. Against *Escherichia coli*, an inhibition zone was also observed around the sample. Against 2 types of the periodontal disease-causing bacteria, an inhibition zone was also observed around each sample.

Example 3

Cytotoxicity of Protamine/DNA Complex (a) Sample

A protamine/DNA complex prepared according to the same process as in Example 2 (a) was used. The ground powders were sieved and powders of 45 to 100 μm were collected and used as a sample. The sample was used after radiation sterilization (1.9 sec, 20 KGy, Dynamitron, by IBA Industrial).

(b) Evaluation Method for Cytotoxicity

As a cell, a publicly available mouse-derived fibroblast L-929 was used. A cell suspension of $1\times10^4$ cell/mL was prepared with an α-MEM medium (Dulbecco's modified Eagle's medium) containing 10% fetal bovine serum (by Introgen Therapeutics Inc.), and dispensed 2 mL each to each well of a 6-well multiplate. After incubation at 37° C. for 24 hours, the culture fluid was exchanged with 2 mL of α-MEM mediums containing 1, 2, or 4 mg of the sample, and incubation was conducted another 5 days. After the 5-day incubation, the culture fluid was exchanged with 2 mL of a medium containing 0.4 mL of CellTiter 96(R) Aqueous MTS (by Promega KK), and after incubation at 37° C. for 2 hours, the absorbance at 492 nm was measured to determine the cell viability (the ratio to the control group to which no sample was added). The test was repeated with n=5, and the results were averaged.

(c) Test Results

The results of the cytotoxicity test are shown in Table 2. The cell viability in a concentration of 0.5 to 2.0 mg/mL was very high, and it was confirmed that the protamine/DNA complex did not exert cytotoxicity.

TABLE 2

Results of cytotoxicity tests

| Sample | Sample concentration (mg/ml) | Cell viability (%) |
|---|---|---|
| Protamine/DNA complex | 0.5 | 107.6 ± 5.3 |
| | 1.0 | 106.0 ± 3.7 |
| | 2.0 | 98.5 ± 2.8 |

Example 4

Evaluation of Bio-Compatibility of a Protamine/DNA Complex (a) Sample

A protamine/DNA complex prepared according to the same process as in Example 2 (a) was used. The protamine/DNA complex was placed in a Teflon mold with an inner diameter of 5 mm and a thickness of 0.5 mm, covered by Teflon plates from both sides, and freeze-dried to prepare a disk-form sample with a diameter of about 5 mm and a thickness of about 1 mm. The sample was used after radiation sterilization (1.9 sec, 20 KGy, Dynamitron, by IBA Industrial).

(b) Evaluation Method for Biocompatibility

A back region of an SPF rat (specific pathogen free rat, male, 6 week-old) was incised subcutaneously, and a sample was implanted. After a pre-determined time periods (3 and 10 days), a tissue was taken and subjected to hematoxylin-eosin (HE) staining.

(c) Test Results

Figure 5:
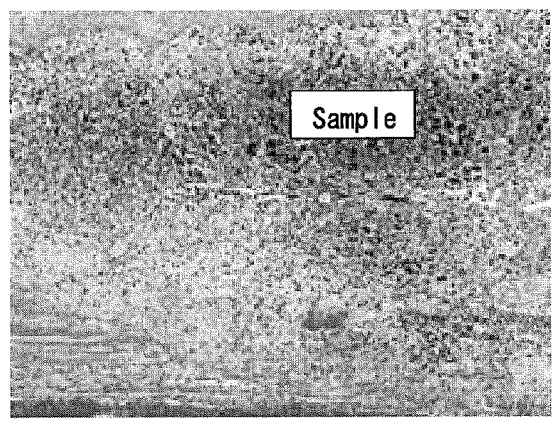
FIG. 5 shows a tissue section on day 3 after implanting a protamine/DNA complex in a rat subcutaneously.
Figure 6:
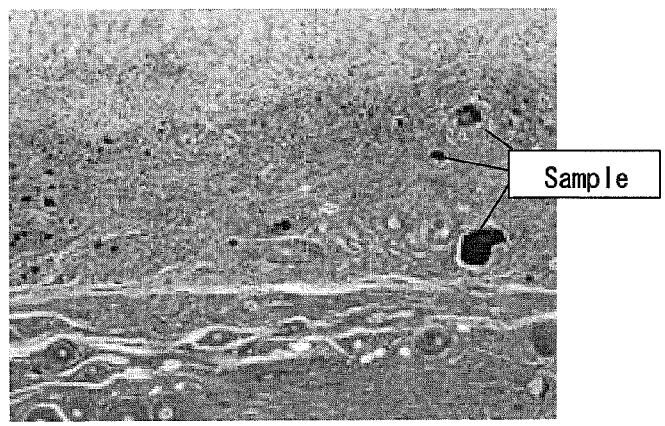
FIG. 6 shows a tissue section on day 10 after implanting a protamine/DNA complex in a rat subcutaneously.

The resulted tissue pictures are shown in FIGS. 5 and 6. On day 3 from the starting point of the implant treatment, the sample was surrounded by granulation tissue in subcutaneous tissue, and completely demarcated from normal tissues. The implanted sample was fragmented and existed as small pieces (fragments), and slight neutrophil infiltration was recognized around the small pieces. These findings was considered to result from very weak biological acute inflammatory reaction caused by the implanted sample. Occurrence of infection by the sample implanting was not recognized. On day 10 from the starting point of the implant treatment, the subcutaneous implanted part was completely replaced with granulation tissue. Fragmentation of the implanted sample was advanced by a phagocytosis reaction of multinucleated giant cells and presented histologically a typical foreign-body granuloma appearance. From advanced fibrosing in the granulation tissue, it was presumed that the implanted material would disappear in the future and the reaction would complete with entire organization (replacement to fibrous connective tissue). Histological observation on days 3 and 10 of the implanting suggested that the compatibility of the protamine/DNA complex thus used to a living body was extremely good.

Example 5

Evaluation of Protamine/DNA/Carbonate Apatite Complex as Scaffold Material for Proliferating Osteoblasts (a) Sample To a protamine/DNA complex (undried) prepared according to the same process as in Example 2 (a), carbonate apatite in an amount of 60% based on weight and an appropriate amount of water were added and mixed, which was formed into a disk-form sample with an inner diameter of 5 mm and a thickness of 1 mm using a Teflon mold.

(b) Evaluation Method

The sample was immersed in an α-MEM medium, to which an MC3T3-E1 cell was inoculated. After incubation for 6 hours, the sample was taken out and the surface thereof was washed with a PBS buffer. Then, cells attached to the sample were actin stained.

(c) Test Results

Figure 7:
FIG. 7 shows stained osteoblasts attached on the surface of a protamine/DNA/carbonate apatite complex.

A graphic image of fluorescently-stained cells is shown in FIG. 7. A scene of cells attaching to surfaces of the protamine/DNA/carbonate apatite complex was recognized, and it was confirmed that the complex functioned as a scaffold for proliferating osteoblasts.

Example 6

Implanting Test of Protamine/DNA/Carbonate Apatite Complex in Rat Cranial Defect Part (a) Sample To a protamine/DNA complex (undried) prepared according to the same process as in Example 2 (a), carbonate apatite in an amount of 60% based on weight was added and mixed together with an appropriate amount of water, which was then formed into a disk-form sample with an inner diameter of 5 mm and a thickness of 1 mm using a Teflon mold.

(b) Evaluation Method

A bone defect was prepared in the cranium of an SP rat (specific pathogen free rat, male, 6 week-old) using a trephine bar (diameter 5 mm). A sample was implanted and a rat was sacrificed at month 1, 1.5 and 2 from the starting point of the implant treatment, and respective tomographic images at the cranial defect part were taken by an X-ray CT apparatus (ScanXmate-RBO90SS150; by Comscantecno Co., Ltd.) to check whether or not the bone regeneration was advancing.

(c) Test Results

Figure 8:
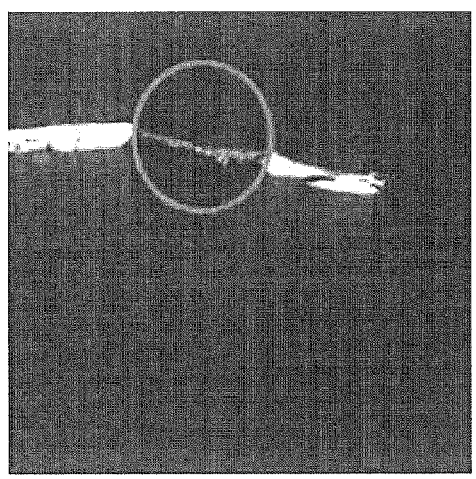
FIG. 8 is X-ray CT graphic images of a rat cranial defect part at 1 month after implanting a protamine/DNA/carbonate apatite complex, wherein (A) is a X-ray CT graphic image of the rat cranial defect part in the sagittal section, and (B) is a X-ray CT graphic image of the rat cranial defect part in the coronal section.
Figure 8:
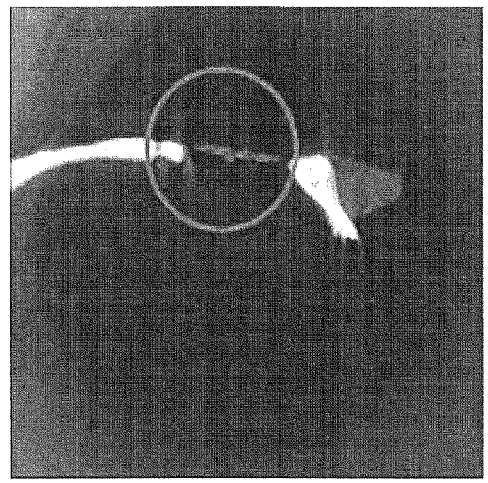
Figure 9:
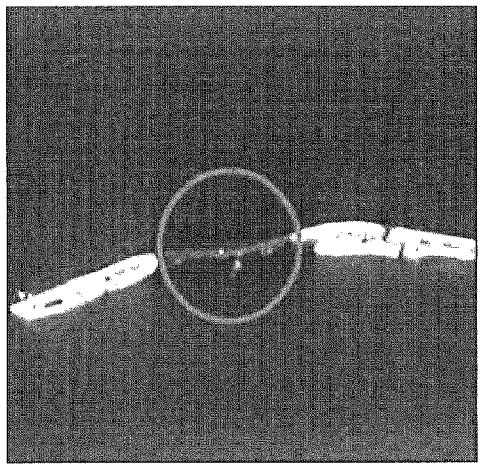
FIG. 9 is X-ray CT graphic images of a rat cranial defect part at 1.5 months after implanting a protamine/DNA/carbonate apatite complex, wherein (A) is a X-ray CT graphic image of the rat cranial defect part in the sagittal section, and (B) is a X-ray CT graphic image of the rat cranial defect part in the coronal section.
Figure 9:
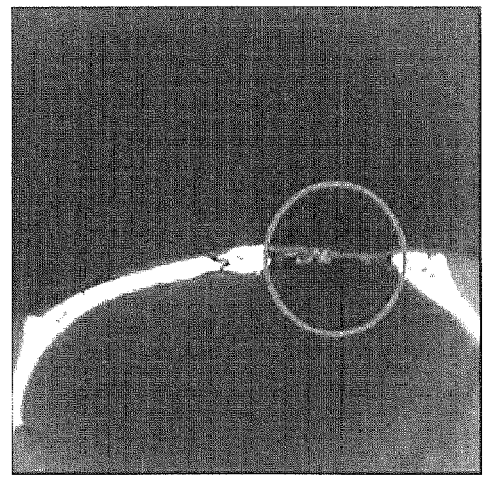
Figure 10:
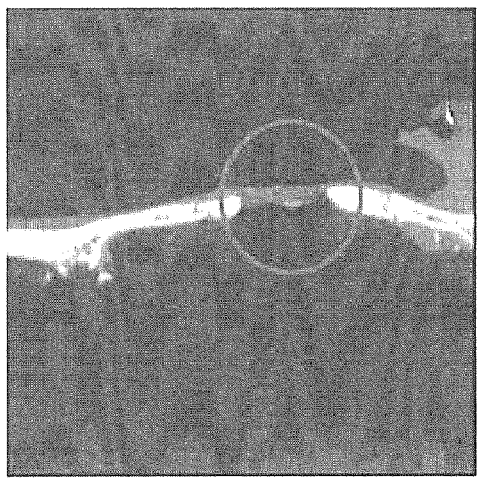
FIG. 10 is X-ray CT graphic images of a rat cranial defect part at 2 months after implanting a protamine/DNA/carbonate apatite complex, wherein (A) is a X-ray CT graphic image of the rat cranial defect part in the sagittal section, and (B) is a X-ray CT graphic image of an X-ray CT image of the rat cranial defect part in the coronal section.
Figure 10:
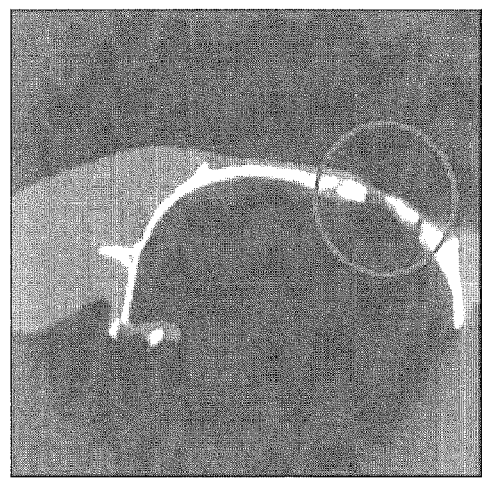

At month 1 from the starting point of the implant treatment, CT scan images in the sagittal section and in the coronal section exhibited an opaque image of a newly formed bone-like tissue (FIGS. 8 (A) and (B)). At month 1.5 from the starting point of the implant treatment, there was no recognizable difference in an image in the sagittal section (FIG. 9 (A)) from that at month 1, but in an image in the coronal section advancement of the formation of the bone-like tissue from that at month 1 was observed (FIG. 9 (B)). At month 2 from the starting point of the implant treatment, in an image in the sagittal section (FIG. 10 (A)), the formation of a bone-like tissue from the peripheral areas of the implanted sample toward the center was recognized, and also in an image in the coronal section further formation of a bone-like tissue compared to that at month 1.5 was observed (FIG. 10 (B)).

The invention claimed is:

1. A medical or dental material for osteogenesis, in the form of paste, which comprises a complex of a protamine with a DNA electrostatically bound with the protamine,
wherein the medical or dental material has antimicrobial activity, insolubility in water and formability for guiding or promoting osteogenesis, and
wherein the DNA has a molecular weight between 300 bp and 7,000 bp.

2. A medical or dental material according to claim 1, wherein the complex includes calcium phosphate.

3. A medical or dental material according to claim 1, which carries a bone morphogenetic protein or a growth factor.

4. A medical or dental material according to claim 1, which has formability to fill a bone defect as a bone filling material for guiding or promoting osteogenesis.

5. A medical or dental material according to claim 1, which is molded to form a membrane for guiding paradentium regeneration or to form a shape selected from the group consisting of a string, a rod, a spherical and a disk for guiding osteogenesis.

* * * * *